May 22, 1973 D. L. ARMSTRONG Plant Pat. 3,340
ROSE PLANT
Filed May 5, 1971
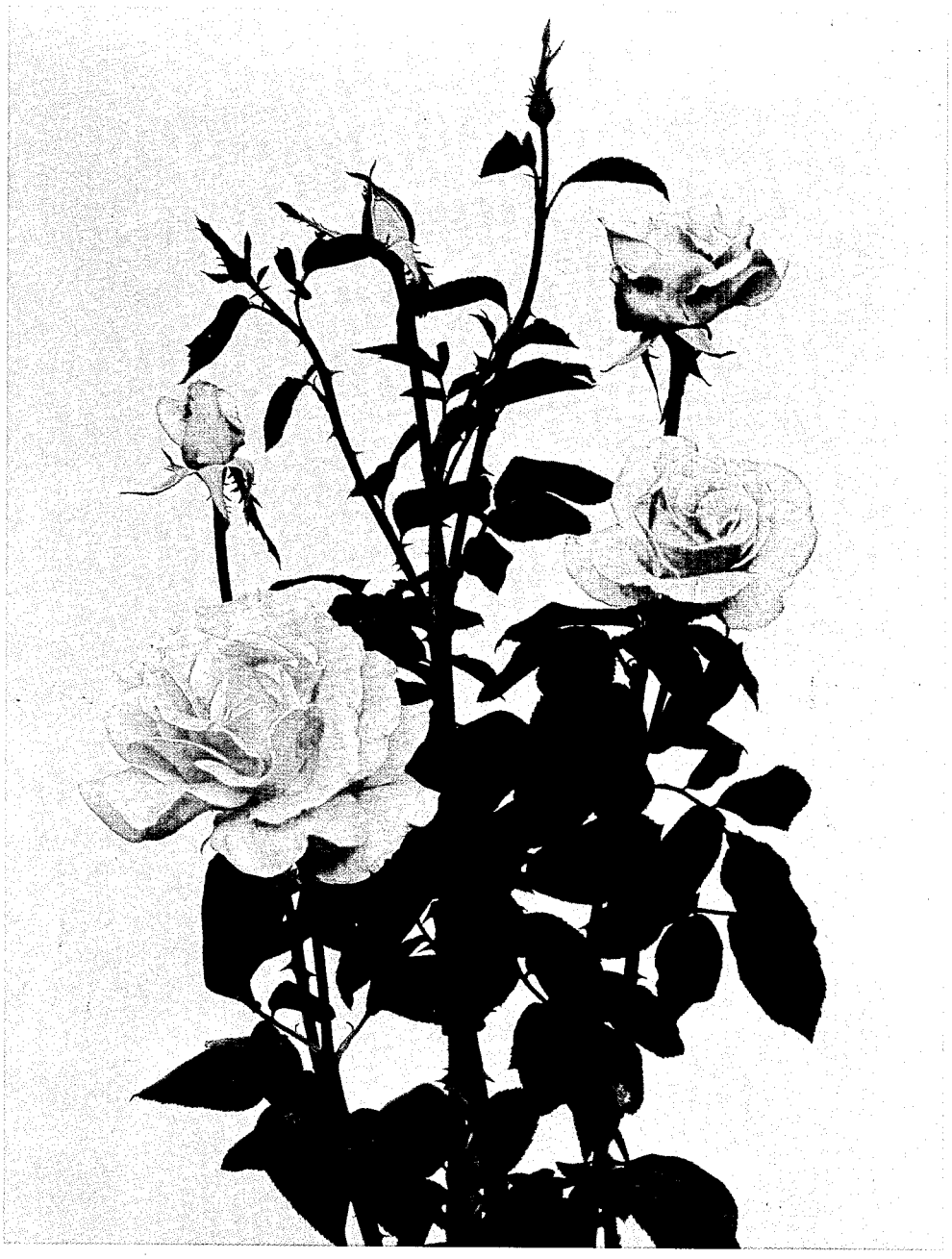

United States Patent Office

Plant Pat. 3,340
Patented May 22, 1973

3,340
ROSE PLANT

David L. Armstrong, Upland, Calif., assignor to Armstrong Nurseries, Inc., Ontario, Calif.

Filed May 5, 1971, Ser. No. 140,543
Int. Cl. A01h 5/00
U.S. Cl. Plt.—19 1 Claim

ABSTRACT OF THE DISCLOSURE

A hybrid tea rose plant which bears average to large size purplish pink blooms on rather strong moderately long stems. Most stems bear a single bloom, though some may bear four or five in an irregular cluster. The plant foliage is abundant, with moderately large leathery but not glossy leaves and longer-than-average peduncles: somewhat better than average resistance to mildew. The buds are quite long, either pointed or urn-shaped, and open into blooms which comprise quite broad petals, especially towards the center. Fragrance: moderately strong tea rose.

This invention relates to a new class of hybrid tea rose. The plant is a seedling of the tall bushy outdoor type, cultivated for cut flowers primarily and for garden decoration. It was propagated by David L. Armstrong in Ontario, Calif., having as its seed parent "Charlotte Armstrong" and, as its pollen parent, "Duet." It holds its distinguishing characteristics through succeeding propagations by budding.

The new variety bears its flowers usually singly on normal to strong, medium to long stems. From four to five or more blooms may sometimes be carried on one stem, however, in an irregular cluster. The plant blooms freely outdoors, and almost continuously during the growing season. Its blooms have a moderate to strong tea fragrance.

The new variety differs from its seed parent, Charlotte Armstrong, in several ways, including the following:

The habit of growth is substantially less spreading than that of the Charlotte Armstrong plant.

The peduncles of the new variety carry substantially fewer stipitate glands than do those of its seed parent.

As to the flower, the petals, especially the inner petals, are substantially broader than in the flowers of the Charlotte Armstrong variety. The fragrance of the bloom is a moderate to strong tea rose aroma, whereas the seed parent, Charlotte Armstrong, has flowers with little or no fragrance.

Distinctions between the new cultivar and its pollen parent, Duet, include the following:

The habit of growth is more upright in the new cultivar than in its pollen parent, Duet.

The peduncles of this new variety are substantially longer than those of Duet, and the foliage of this new variety is not significantly glossy, whereas the foliage of Duet may be semi-glossy to glossy.

The flowers of the new variety display a lighter shade of pink, and do not display as great a disparity between the inner surfaces and the outer surfaces of the petals as is noted in Duet. The color of the Duet flower is typically light red to very dark pink with yellow undertone on the outer surfaces. Its inner surfaces display a lighter pink, strongly influenced by yellow at the base. In comparison, the blooms of the new variety are of a definitely purplish pink hue, although they also comprise yellow.

The fragrance of the flowers of this new variety is substantially greater than the blooms of the pollen parent.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is of longer than average length but of average caliper, being erect and usually smooth, but with a few gland-tipped cilia. The color is near Strong Yellow Green, 2.5GY 6/8, overlaid with near Light Olive, 7.5Y 5/5, in areas exposed to the sun.

Before the calyx breaks, the bud is medium in size, medium length, and ovoid in form.

As the calyx breaks, the color is near Moderate Red, 2.5R 4/10. The inner surface of the sepals carries a fine, woolly tomentum.

The margins of alternate sepals are lined with a fine woolly tomentum; margins of others with several to many small stipitate glands and small slender foliaceous parts.

The outside surface of the sepals is usually smooth.

The sepals are usually with foliaceous appendages extending to one-quarter to one-half of the sepal length.

As the first petal opens, the bud is average to large in size, long and usually urn-shaped. The color on both the inside and the outside of the petal is near Deep Purplish Pink, 7.5RP 6/12. The bud opens up well and is not retarded or prevented from opening by cold, hot, wet, or dry weather.

*Bloom*

The size of the bloom when fully open is average to large, ranging from 4 to 5 inches. The petalage is double, with from 25 to 30 petals arranged irregularly, plus 4 to 8 petaloids. The bloom is very high centered at first, becoming flat to high centered.

At first the petals are tightly cupped, with tips refluxed outward, becoming later at maturity loosely flat to cupped, with tips reflexed outward.

The intermediate petals of both the newly open and three days open flower are usually reflexed outwardly along the apex. The outside petals of both the newly open and three days open flower are usually also reflexed outwardly along the edges.

The petals are moderately thick, and are leathery in texture, with inside velvety and outside satiny. The outside petals are broadly obovate, with apex flat, and sometimes with 2 to 3 notches. Both the intermediate and inside petals are also obovate, but with apex rounded to flat, and sometimes with 1 to 3 notches. The colors may be modified by being shaded and/or washed with other colors.

The paragraphs immediately following describe color values observed in a flower newly opened in the month of September. The plant had been grown outdoors, in Ontario, Calif.

The outer surface of the outside petal is between Deep Purplish Pink, 5RP 6/10 and Deep Purplish Pink, 7.5RP 6/12, with a small area at the base of the petal near Brilliant Greenish Yellow, 7.5Y 9/8. The inner surface of the outside petal is near Deep Purplish Pink, 7.5RP 6/12, with a small area at the base of the petal near Brilliant Greenish Yellow, 7.5Y 9/8.

Both the outer surface and the inner surface of the intermediate petal is between Deep Purplish Pink, 7.5RP 6/12, and Strong Purplish Red, 7.5RP 5/12, with a small area at the base of the petal near Brilliant Greenish Yellow, 7.5Y 9/8.

The coloring of the inner petal is the same as that of the intermediate petal.

The paragraphs immediately following describe the color values observed in a bloom which had been open for three days, outdoors, in the month of September. The plant had been grown outdoors, in Ontario, Calif.

The outer surface of the outside petal was between Moderate Purplish Red, 5RP 5/10, and Deep Purplish Pink, 7.5RP 6/12. The inner surface was between Deep Purplish Pink, 5RP 6/10, and Strong Purplish Pink, 7.5RP 7/10.

The inside petal was characterized by the same color values as the outside petal, both on the outer surface and on the inner surface.

The general color effect of the newly opened flower is between Deep Purplish Pink, 7.5RP 6/12, and Strong Purplish Red, 7.5RP 5/12. The bloom after being three days open gives a general color effect which is between Deep Purplish Pink, 5RP 6/10, and Strong Purplish Pink, 7.5RP 7/10. The petals drop off cleanly, and are not particularly affected in this respect by cold, hot, wet, or dry weather.

The flower on the bush in the garden persists for from 3 to 4 days in the month of August, in the locality named. Cut roses grown outdoors and kept at living-room temperatures will last from 2 to 4 days in the month of August.

*Reproductive organs*

Stamens: The stamens are average in number, regularly arranged about the pistils, a few of them being mixed with petaloids.

Filaments: The filaments are short to medium length, being 5 to 10 mm. in length, and near Vivid Yellow, 5Y 8/12, in color. Most are with anthers.

Anthers: The anthers are small to medium size, all opening approximately at once. On both the upper and lower side the margins are near Strong Orange Yellow, 10YR 7/10, and the central area is near Pale Orange Yellow, 7.5YR 9/4.

Pollen: The pollen is moderate in quantity, near Strong Orange Yellow, 7.5YR 7/11, in color.

Pistils: The pistils are approximately 75 in number, this being average.

Styles: The styles are uneven, short to average length, thin caliper, and bunched. The upper one-third of the style is near Strong Red, 2.5R 5/12; the remainder near Pale Orange Yellow, 7.5YR 9/4.

Stigma: The stigma is near Light Orange, 5YR 8/7, in color.

Ovaries: The ovaries usually are all enclosed in the calyx.

Hips: No hips were observed on plants grown at Ontario, Calif.

Sepals: The sepals are permanent. They are spear-shaped and recurved, more or less. The color, both inside and outside, was not significant.

Seeds: No seed was produced.

*Foliage*

The compound leaves usually comprise three to seven leaflets. They are abundant, medium to large in size, leathery and non-glossy in texture. The leaflets are oval, with apex acute, base round, and margin simply serrate.

The mature foliage displays on its upper surface a color between Moderate Olive Green, 5GY 4/3, and Grayish Olive Green, 5GY 3/2. The under surface is near Moderate Yellow Green, 7.5GY 5/7.

The young foliage on its upper surface is near Moderate Olive Green, 7.5GY 4/4, and on its under surface is near Moderate Yellow Green, 7.5GY 5/7.

The rachis is average in size, grooved on the upper side, with a few stipitate glands on the edges. The under side is smooth, except for some stipitate glands and a few prickles.

The stipules are medium-length and medium-width, with short points, turning out at an angle of more than 45°.

The plant displays a more than average resistance to mildew, when compared with other varieties now in commerce under comparable conditions, when grown at Ontario, Calif.

*Growth*

The plant is of upright-spreading habit, much branched. It displays a vigorous growth. The canes are medium to heavy in caliper.

The main stems are near Moderate Yellow Green, 7.5GY 5/7, in color. They bear several large prickles which are medium-length, hooked slightly downward, with short to medium-length base. Their color is near Brownish Orange, 5YR 5/8. There are a few small prickles, and their color is the same as that of the large prickles. There are no hairs.

The branches are near Moderate Yellow Green, 5GY 5/6, in color. They carry several large prickles which are medium-length, hooked slightly downward, with short to medium-length base. Their color is near Light Orange, 5YR 8/7. There are a few small prickles, and their color is the same as that of the large prickles. There are no hairs.

New shoots have a color near Moderate Yellow Green, 5GY 5/6. There are a few large prickles, short to medium-length, hooked slightly downward, with short base. Their color is near Brownish Orange, 5YR 5/8. There are a few small prickles, and their color is the same as that of the large prickles. There are no hairs.

I claim:

1. A new variety of hybrid tea rose plant substantially as shown and described in the foregoing specification, and displaying a combination of characteristics including a plurality of the following features: abundant foliage, comprising moderately large leaves which are leathery but not glossy, longer-than-average peduncles with few stipitate glands; elongated buds, either pointed or urn-shaped; opening into high-centered, well-balanced flowers of moderately strong tea rose fragrance, the petals of which flowers, especially towards the center of the bloom, are notably broad; said plant having a somewhat better than average resistance to mildew.

No references cited.

ROBERT E. BAGWILL, Primary Examiner